(12) United States Patent
Haro (10) Patent No.: US 7,935,337 B2
(45) Date of Patent: May 3, 2011

(54) METHOD OF THERAPY FOR DEGENERATIVE INTERVERTEBRAL DISCS

(75) Inventor: Hirotaka Haro, Tokyo (JP)

(73) Assignees: Hiromichi Komori, Tokyo (JP); Hirotaka Haro, Tokyo (JP)

( * ) Notice: Subject to any disclaimer, the term of this patent is extended or adjusted under 35 U.S.C. 154(b) by 872 days.

(21) Appl. No.: 10/540,521

(22) PCT Filed: Dec. 24, 2003

(86) PCT No.: PCT/JP03/16580
§ 371 (c)(1), (2), (4) Date: Jun. 24, 2005

(87) PCT Pub. No.: WO2004/058296
PCT Pub. Date: Jul. 15, 2004

(65) Prior Publication Data
US 2006/0171939 A1    Aug. 3, 2006

(30) Foreign Application Priority Data

Dec. 25, 2002  (JP) ................. 2002-373527
Jun. 30, 2003  (JP) ................. 2003-187675

(51) Int. Cl.
*A61K 38/46* (2006.01)
(52) U.S. Cl. .................................. 424/94.67
(58) Field of Classification Search ............... 424/94.67
See application file for complete search history.

(56) References Cited

FOREIGN PATENT DOCUMENTS

| EP | 1 111 047 A2 | 6/2001 |
|---|---|---|
| JP | 4-506003 | 10/1992 |
| JP | 10-080283 | 3/1998 |
| JP | 10099084 | 4/1998 |
| JP | 11169176 | 6/1999 |
| JP | 2000-139480 A | 5/2000 |
| WO | WO 90/13561 | 11/1990 |
| WO | WO 97/40157 | 10/1997 |

OTHER PUBLICATIONS

Avakyan, "Effect of the Proteolytic Enzymes Trypsin and Chymopsin on an Intervertebral Disk Under Experimental Conditions," *Chem. Abstr.* 78:23, Abstract No. 106601b (1973).
Benoist et al., "Chemonucleolysis in the Treatment of Sciatica from Herniated Lumbar Disc," *La Nouvelle Presse Médicale* 11(28):2121-2124 (1982).
Buttle, "Chemonucleolysis: An Example of Therapeutic Tissue Damage," *Research Monographs in Cell and Tissue Physiology* 15:269-278 (1988).
Einarson et al., "Chymopapain," *Drug Intelligence and Clinical Pharmacy* 18:560-568 (1984).
Haro et al., "The Role of MMP in Intervertebral Disc Tissues—From Disc Degeneration to Herniated Disc," *Rheumatism* 41(1):44-50 (2001).
Haro et al., "The Role of MMPs in the Resorption Process of Herniated Disc," *Connective Tissue* 33:51-57 (2001).
Haro et al., "Matrix Metalloproteinase-3—Dependent Generation of a Macrophage Chemoattractant in a Model of Herniated Disc Resorption," *The Journal of Clinical Investigation* 105(2): 133-141 (2000).
Haro et al., "Matrix Metalloproteinase-7—Dependent Release of Tumor Necrosis Factor-α in a Model of Herniated Disc Resorption," *The Journal of Clinical Investigation* 105(2):143-150 (2000).
Haro et al., "Up-Regulated Expression of Matrilysin and Neutrophil Collagenase in Human Herniated Discs," *Journal of Spinal Disorders* 12(3):245-249 (1999).
Haro et al., "Chemonucleolysis With Human Stromelysin-1," *Spine* 22(10):1098-1104 (1997).
Haro et al., "Upregulated Expression of Chemokines in Herniated Nucleus Pulposus Resorption," *Spine* 21(14):1647-1652 (1996).
Herron et al., "Does the MMPI Predict Chemonucleolysis Outcome?" *Spine* 13(1):84-88 (1988).
Kudo et al., "Experimental Chemonucleolysis with Chymopapain in Canine Intervertebral Disks," *J. Vet. Med. Sci.* 55(2):211-215 (1993).
Roberts et al., "Matrix Metalloproteinases and Aggrecanase: Their Role in Disorders of the Human Intervertebral Disc," *Spine* 25(23):3005-3013 (2000).
Sagona et al., "Pretreatment Serum Levels of IgE to Chymopapain in Reactive Patients," *Annals of Allergy* 55:674-677 (1985).
Troisier et al., "The Treatment of Lumbosciatica by Intra-discal Injection of Proteolytic Enzymes (Nucleolysis)," *La Nouvelle Presse Médicale*, 9(4)227-230 (1980).
International Search Report for PCT/JP2003/016580, May 11, 2004.
Haro et al. "Up-Regulated Expression of Matrilysin and Neutrophil Collagenase in Human Herniated Discs", Journal of Spinal Disorders (1999) vol. 12, No. 3, pp. 245-249.
Supplementary European Search Report dated Nov. 13, 2007.
Japanese Office Action issued Dec. 15, 2009, in JP 2005-509747.

*Primary Examiner* — San-ming Hui
*Assistant Examiner* — Paul Zarek
(74) *Attorney, Agent, or Firm* — Sughrue Mion, PLLC (57) ABSTRACT

To treat diseases accompanied by degenerative intervertebral discs, in particular, disk herniation, lumbar pain, discopathy and osteoarthritits of the spine, it is intended to provide a drug for administering a human-origin protease directly to an affected part of such a disease accompanied by degenerative intervertebral discs. As the human-origin protease, use can be made of MMP-3, MMP-7, etc.

2 Claims, 14 Drawing Sheets

Fig. 4 Canine hernia specimen (HE)

After NS injection

After MMP-7 injection
Macro, Safranin O staining

Fig. 11

Fig. 12 Safranin O staining after NS injection (Macro) (x2) (x10)

METHOD OF THERAPY FOR DEGENERATIVE INTERVERTEBRAL DISCS

TECHNICAL FIELD

The present invention relates to an agent for treating diseases associated with degenerative intervertebral disc which comprises a human-derived protease as an active ingredient. The agent is directly administered to the affected part of a disease associated with degenerative intervertebral disc, and is effective for disc herniation, lumbar pain, discopathy and spondylosis and the like, by promoting natural resorption of the herniated disc.

BACKGROUND ART

Intervertebral discs, the disc-shaped cartilaginous bodies interposed between adjacent vertebrae, are each composed of an outer annulus fibrosus surrounding the inner nucleus pulposus, and comprise cartilaginous components such as proteoglycans, aggrecans, type II collagen and the like. Intervertebral discs lose their elasticity due to reduction of water content in discs occurring primarily as a result of aging, with concomitant loss of cartilaginous components and build-up of fibrous tissue, which leads to destruction of the double structure of the inner nucleus pulposus and the outer annulus fibrosus. This change is referred to as "degenerative intervertebral disc". Degenerative intervertebral disc progresses with increasing age beginning in the third decade, with degeneration of virtually all intervertebral disc tissue occurring by age 70. Herniated disc is caused when degenerative nucleus pulposus ruptures the fragile fibrous tissue and protrudes into the spinal canal, compressing against the nerve root and cauda equina and producing pain or paralysis. Lumbago can also be caused by abnormal bone metabolism, external injury, tumor or the like, but usually results from degeneration of intervertebral discs.

Magnetic Resonance Imaging (MRI) is widely used for diagnosis of degenerative intervertebral discs. Because it does not involve exposure as with X-rays, it can be used for frequent examination. Sequential imaging has confirmed a natural resorption mechanism whereby the volume of herniated discs decreases with time. Also, use of the contrast agent gadolinium-diethylenetriamine pentaacetic acid (Gd-DTPA) has shown abundant neovascularization in herniated discs when an imaging effect is seen in the herniated intervertebral disc tissue, suggesting that more natural resorption is occurring. This principle can be utilized for diagnosis and prognosis.

Immunohistological examination of extracted human surgical samples of herniated disc masses has revealed increased neovascularization and infiltration of numerous inflammatory cells consisting primarily of macrophages, in the cartilage matrix of herniated disc masses (Haro et al., Spine 21 (1996), 1647-1652). It has been confirmed that the infiltrating macrophages and intervertebral disc chondrocytes abundantly express the matrix metalloproteinases (MMPs) MMP-3 and MMP-7 (Haro et al., Spine 22 (1997), 1098-1104 and Haro et al. J. Spinal. Disorders 12 (1999), 245-249). MMPs are enzymes which function mostly in the neutral range and are physiologically expressed intraarticularly and in the intervertebral disc tissue. Proteoglycans and aggrecans, major cartilage tissue components, are the substrates of MMP-3 and MMP-7. It is therefore assumed that MMP-3 and MMP-7 play important roles in the degradation and resorption of herniated discs.

When wild-type mouse intervertebral discs are co-cultured with active macrophages, reduction in intervertebral disc mass is greater than with co-culturing of macrophages and intervertebral discs derived from MMP-3 deficient mouse. Experiments using wild-type mice and MMP-3 deficient mice have confirmed that MMP-3 has a chemotactic effect on macrophages causing them to migrate toward the intervertebral discs (MMP-3 functions as a chemotactic factor for macrophages) (Haro et al., J. Clin. Invest. 105(2) (2000), 133-141).

MMP-7 elicits the inflammatory cytokine TNF-α, and TNF-α has been reported to promote production of MMP-3 in intervertebral disc cells (Haro et al., J. Clin. Invest. 105(2) (2000), 143-150). However, it has never been attempted to use human-derived proteases such as MMP-3 and MMP-7 expressed in human herniated discs as therapeutic agents.

Surgical treatment for herniated discs ordinarily attempts to achieve nerve decompression by removal of the herniated disc mass. However, because the condition is common among adolescent and middle age groups and relatively frequent among sport athletes, a non-invasive treatment has been sought in order to avoid surgery.

Treatment by injection of enzymes such as plant-extracted chymopapain into herniated discs is already practiced in the U.S. and Europe, but immunoreaction and neurotoxicity have been reported. Also, although it has been reported that injection of chymopapain into herniated disc sites gradually restores herniated disc cavities produced by proteolysis, this is attributed to hyperplasia not of the cartilaginous matrix but of fibrous connective tissue. Histological observations of chymopapain-injected canine discs have reportedly revealed replacement of the nucleus pulposus center with fibrocartilaginous tissue (Kudo et al., J. Vet. Med. Sci. 1993, April, 55(2) 211-5). According to experimentation by the present inventors, cases where chymopapain was injected into canine herniated discs showed degradation of the cartilaginous matrix throughout the entire nucleus pulposus and annulus fibrosus, with the surviving chondrocytes markedly reduced and extensively damaged. Thus, lysis of herniated disc with chymopapain is believed to either reduce or eliminate intervertebral disc regenerative capacity. Since chondrocytes maintain their function while suspended in the matrix, the matrix is indispensable for intervertebral disc regeneration. Consideration of these publicly known facts together with knowledge confirmed by the present inventors suggests that in the conventional methods in which proteases are directly administered to herniated disc sites for removal of degenerative nucleus pulposus, it is difficult to sustain the matrix which is required to support the intervertebral disc regenerative capacity of chondrocytes.

DISCLOSURE OF THE INVENTION

Surprisingly, it was discovered that injection of MMPs, types of human-derived proteases, into herniated discs promotes resorption of herniated discs but does not injure normal chondrocytes. Specifically, it was possible to degrade herniated discs while maintaining intervertebral disc regenerative capacity. As mentioned above, the matrix is absolutely essential for maintaining chondrocyte function. The present invention is based on the revolutionary knowledge that injection of MMPs, which are human-derived proteases, into herniated disc promotes selective resorption of the herniated disc while preserving normal chondrocytes. The invention provides a completely novel herniated disc treatment which does not entail the risk of injury to normal chondrocytes as occurs when using hitherto known chymopapain.

It is an object of the present invention to provide an agent for treating diseases associated with degenerative intervertebral disc which comprises as an active ingredient a human-derived protease believed to contribute to natural human herniated disc resorption, and which is directly administered to the degenerative intervertebral disc. The invention further provides a treatment method for disorders associated with degenerative intervertebral disc whereby the human-derived proteases are directly administered to the degenerative intervertebral disc. The target disorders for the treatment of the invention are conditions associated with degenerative intervertebral disc and include herniated disc, lumbago, discopathy and spondylosis.

The aforementioned MMP-3 and MMP-7 may be mentioned as substances believed to contribute to resorption of herniated disc based on research to date. A similar effect is thought to be exhibited by MMP-8, MMP-13, MT1-MMP (MMP-14) and aggrecanase. MMP-3 (E.C.3.4.24.17), also known as stromelysin-1 or transin, degrades fibronectin, laminin, proteoglycan and various collagens. MMP-7 (E.C.3.4.24.33), also known as matrilysin or PUMP, degrades type IV and type X collagen, elastin, fibronectin, gelatin, laminin and proteoglycan. MMP-8 (E.C.3.4.24.34), also known as collagenase-2 or neutrophil collagenase, degrades type I collagen preferentially over type II or type III collagen. MMP-13 is also known as collagenase-3 and is highly specific for type II collagen. MT1-MMP (membrane type-1 matrix metalloproteinase), also known as MMP-14, activates pro-MMP-2 and pro-MMP-13. Aggrecanase belongs to the ADAM-TS (a disintegrin and metalloproteinase-thrombospondin) family and degrades cartilage aggrecan.

These proteases have recently been produced and provided by recombinant technology. The present inventors have utilized and confirmed the efficacy of these proteases by injection into conditions associated with degenerative intervertebral disc, such as herniated disc. In addition, it was confirmed that these human-derived proteases do not carry the risk of injuring normal chondrocytes which is exhibited by chymopapain, and the present invention was thereupon completed.

BEST MODE FOR CARRYING OUT THE INVENTION

The present invention provides an agent for treating diseases associated with degenerative intervertebral disc which comprises as an active ingredient one or more human-derived proteases and is administered directly to the site of the condition associated with degenerative intervertebral disc. In particular, it is an agent for treating herniated disc, lumbago, discopathy and spondylosis. The proteases as the active ingredients are extracellular matrix proteases such as, for example, MMP-3, MMP-7, MMP-8, MMP-13, MT1-MMP (MMP-14) and aggrecanase.

The agent for treating diseases associated with degenerative intervertebral disc according to the invention is directly administered to, for example, a herniated disc site. The method of administering the agent of the invention may be administration into the intervertebral disc near the hernia. In disc puncture, for example, a puncture needle is advanced subcutaneously under fluoroscopic control. The inner cylinder is then advanced in the direction of the protruded disc for selective puncture of the protruded herniated disc, and the drug agent of the invention is injected. It may also be administered by epidural space injection. Administration of the agent of the invention in this manner can promote natural resorption of the herniated disc.

The use of an agent for treating diseases associated with degenerative intervertebral disc according to the invention requires diagnosis wherein a neural symptom such as radiculopathy, cauda equina syndrome or myelopathy is observed and the condition of nerve compression and the site and severity of the degenerative intervertebral disc, such as herniated disc, is confirmed by magnetic resonance imaging (MRI). Discographic examination is also important for imaging of the herniated disc mass at the site to be treated, in order to accurately judge the site and extent of the herniated disc.

Thus, one mode of the invention is a treatment method for herniated disc wherein a patient suspected of having a degenerative intervertebral disc, such as a herniated disc, is examined by MRI and discography and, if the patient is found to have a degenerative intervertebral disc such as a herniated disc, a human-derived protease of the invention is directly administered to the herniated disc site as appropriate for the pathology, to promote natural resorption of the herniated disc tissue.

The dosage of the agent for treating diseases associated with degenerative intervertebral disc according to the invention will differ depending on the severity of the degenerative intervertebral disc, such as herniated disc, the condition of the patient, the type of protease, etc. The agent for treating diseases associated with degenerative intervertebral disc according to the invention is administered directly to the affected site, and its dosage will normally be in the range of about 1 μg to 100 mg and preferably 100 μg to 1 mg per administration. The frequency of administration is preferably from once to several times, and may be increased depending on the degree of resorption.

EXAMPLES

The present invention will now be explained in greater detail by the following examples, with the understanding that the invention is in no way limited by these examples.

Example 1

Organ Culturing Experiment Using Human Surgical Herniated Disc Specimen

A surgically extracted herniated lumbar disc specimen (stored at 4° C.) was finely sliced, and the wet weight was measured for dispensation into specimen portions of 60-80 μg, which were placed in a 96-well plate. The sample solutions described below were added and culturing was carried out for 24 hours in a $CO_2$ incubator at 37° C.

(1) Control/DMEM medium 200 μl (2) Human recombinant MMP-3 (45 kDa) 20 μg/200 μl (3) Human recombinant MMP-7 (19 kDa) 20 μg/200 μl (4) Human recombinant MMP-3 10 μg+human recombinant MMP-7 10 μg/200 μl (5) Human recombinant MMP-3 20 μg+human recombinant MMP-7 20 μg/200 μl (6) Chymopapain 1, 5, 10, 50, 100, 500 pkt (picoKatal)/200 μl The human recombinant MMP-3 (CHEMICON) and human recombinant MMP-7 (CHEMICON) were dissolved in DMEM medium at 4° C. The chymopapain was used as a positive control, dissolving chymopapain (ICN Biomedicals) in a solution containing 1 mM EDTA, 0.067 mM mercaptoethanol and 5.5 mM cysteine hydrochloride, and carrying out incubation at 25° C., pH 6.2 for 30 minutes for activation prior to addition to the DMEM medium.

Figure 1:
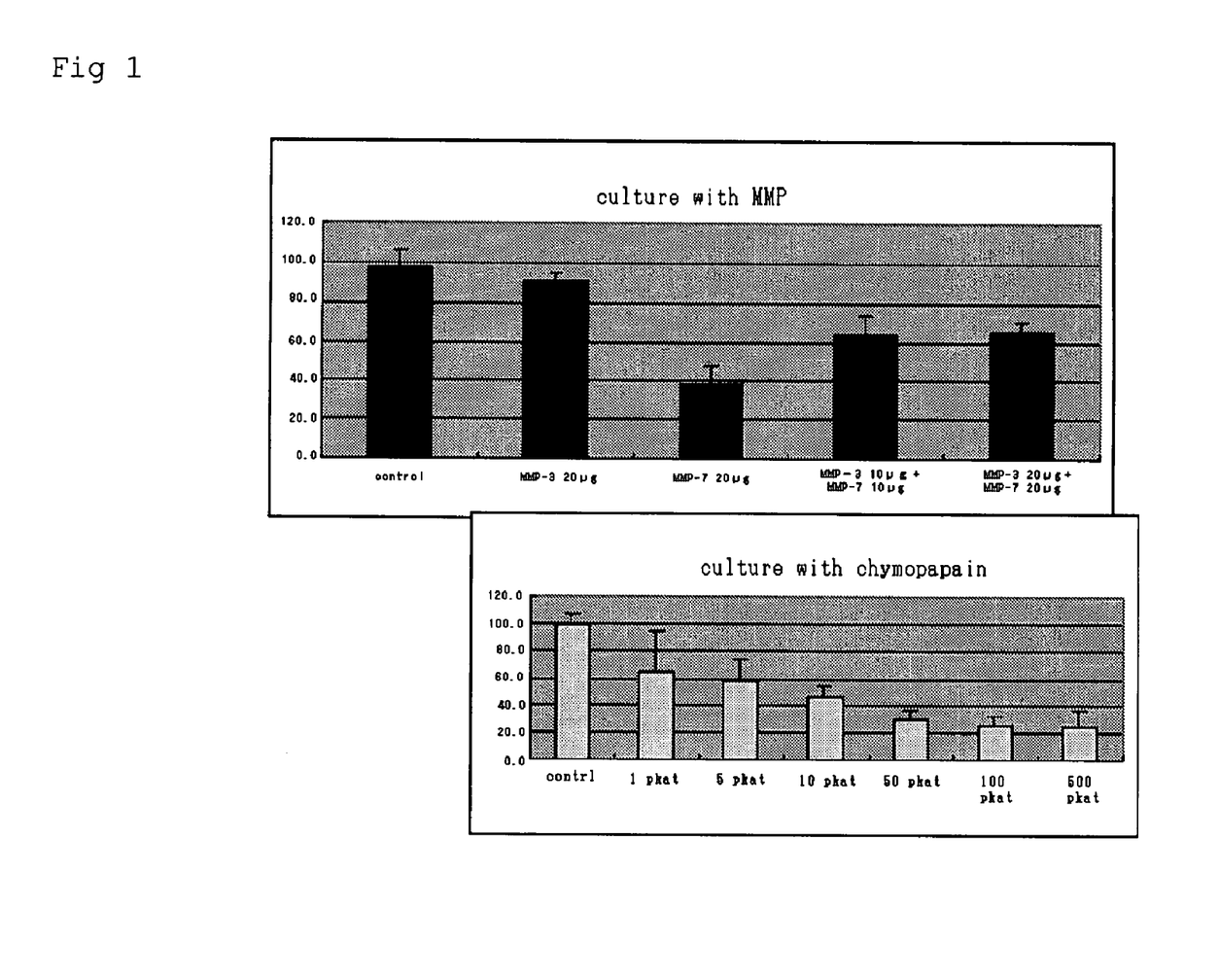
FIG. 1 is a pair of bar graphs showing changes in wet weight of herniated disc specimens cultured with MMP-3, MMP-7, mixtures thereof, chymopapain as a positive control and a control (DMEM medium).

The wet weight of the obtained culture product was measured and statistical calculation was performed. The results are shown in FIG. 1. As clearly seen in FIG. 1, Using MMP-3, MMP-7 or both in combination significantly reduced the wet weight compared to the control.

Figure 2:
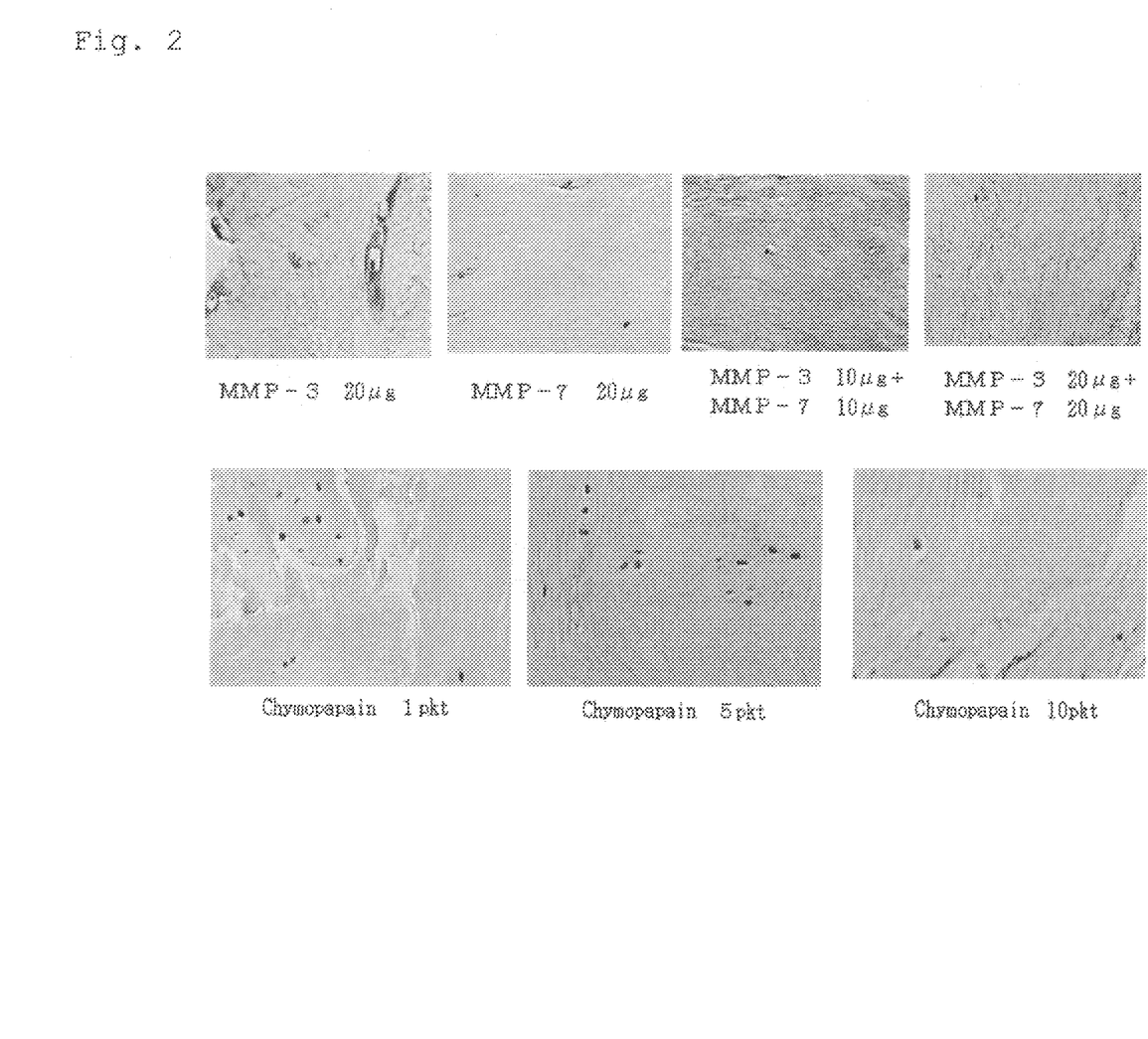
FIG. 2 is a set of photographs showing the results of Safranin O staining of tissue samples obtained by culturing herniated disc specimens with MMP-3, MMP-7, mixtures thereof and chymopapain as a positive control.

Next, the specimen was placed in 4% paraformaldehyde to prepare a tissue sample which was then stained with Safranin O, giving the results shown in FIG. 2. As a result, the cultured organs with addition of MMP-3, MMP-7 or chymopapain exhibited reduction in staining (resorption of herniated disc) which was superior to the control.

Example 2

Experiment for Injection into Rabbit Intervertebral Disc

Japanese white rabbits (3-4 kg) were treated by the procedure described below, and the effects of intervertebral disc injection of drug agents were examined.

1. Premedication treatment was subcutaneous injection of 0.5-1.0 ml/kg of ketamine hydrochloride.

2. The bodies were fixed, and anchored with tape on a line along the ear vein with a 23 G winged needle. Pentobarbital sodium was diluted to half-concentration (0.5 mg/ml) with normal saline and 0.5-1.0 ml/kg was injected in one shot for intravenous anesthesia. Appropriate 1 ml portions were then injected thereafter. The bodies were then shaved with a hair clipper and fixed in the lateral prostrate position (posterior approach).

3. A draping and electric scalpel (air tome) set was used to cut the skin, the subcutaneous area was opened up, and the muscle was separated from the vertebral body and costa to expose the intervertebral discs.

4. The following drug agents were directly injected into the intervertebral discs.

(1) Human recombinant MMP-3 10 μg/100 μl and 40 μg/100 μl (concentrated with Microcon YM-3)

(2) Human recombinant MMP-7 10 μg/100 μl and 40 μg/100 μl (concentrated with Microcon YM-3)

(3) Chymopapain 1 kpt and 5 kpt (Activated by dissolution in solution containing 1 mM EDTA, 0.067 mM mercaptoethanol and 5.5 mM cysteine hydrochloride, and incubation at 25° C., pH 6.2 for 30 minutes)

(4) Control: Normal saline (NS)

A 100 μl portion of the drug agent was injected into the intervertebral disc. Different concentrations of the drug agent were administered at two locations of the intervertebral disc, and the normal saline alone was administered at a single location of the intervertebral disc, after which a marking wire was embedded in the vertebral body.

5. Each layer was closed off with a nylon needle and the rabbits were freed within their cages.

6. One week after injection, 3 ml of ketamine hydrochloride was injected, and after ensuring the line, a 23 G winged needle was fixed at the ear vein, and 3 ml of pentobarbital sodium (1 mg/ml) was administered (total: 5-7 ml).

7. The vertebral body was extracted en bloc and fixed with a 4% formalin solution to prepare a tissue sample.

8. The tissue sample was deparaffinized and stained for 5 minutes with 0.03% Fast Green dissolved in 1% aqueous acetic acid. After washing with 1% aqueous acetic acid, it was further stained for 7 minutes with 0.25% Safranin O.

Figure 3:
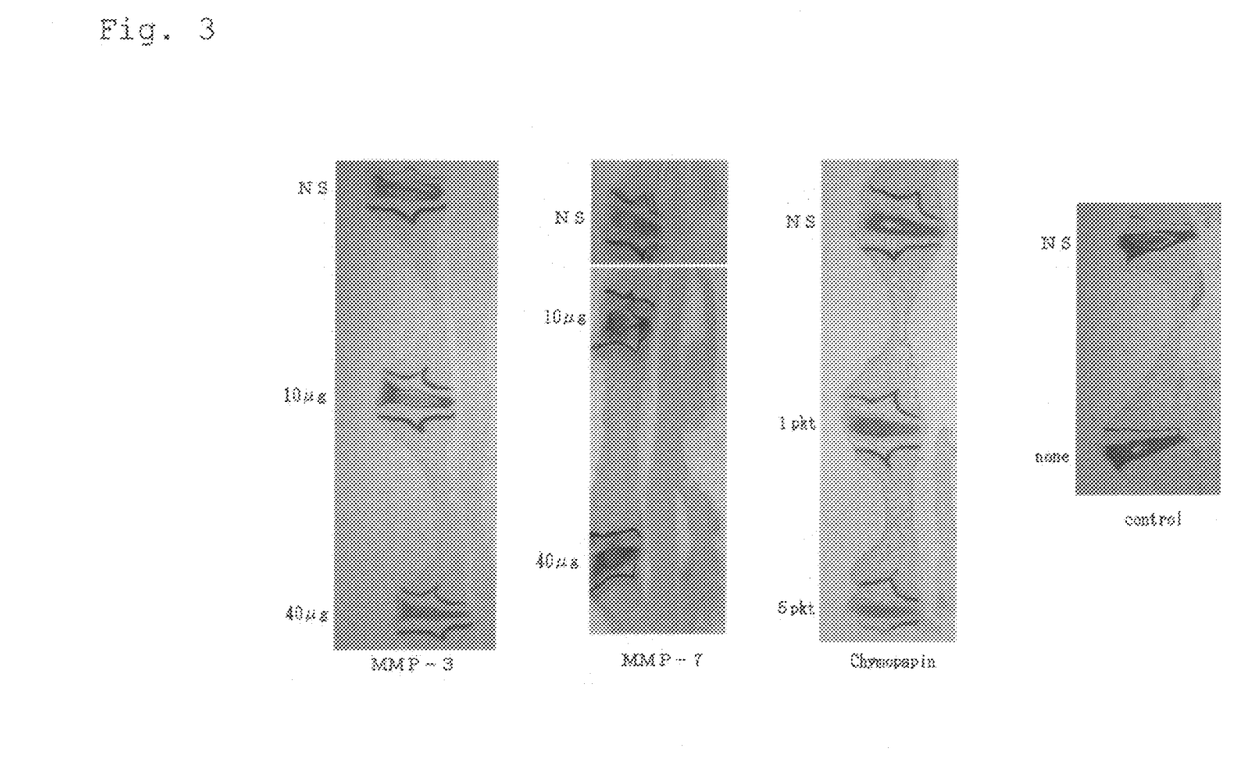
FIG. 3 is a set of photographs showing the results of Safranin O staining of vertebral samples prepared by injecting MMP-3, MMP-7, chymopapain as a positive control and normal saline (NS) into rabbit intervertebral discs and sacrificing after one week.

The results are shown in FIG. 3. The MMP-3, MMP-7 and chymopapain injected groups had significantly reduced staining compared to the control group. The MMP-3 injected group also produced intervertebral disc narrowing.

Example 3

Experiment for Injection into Canine Herniated Disc

Figure 4:
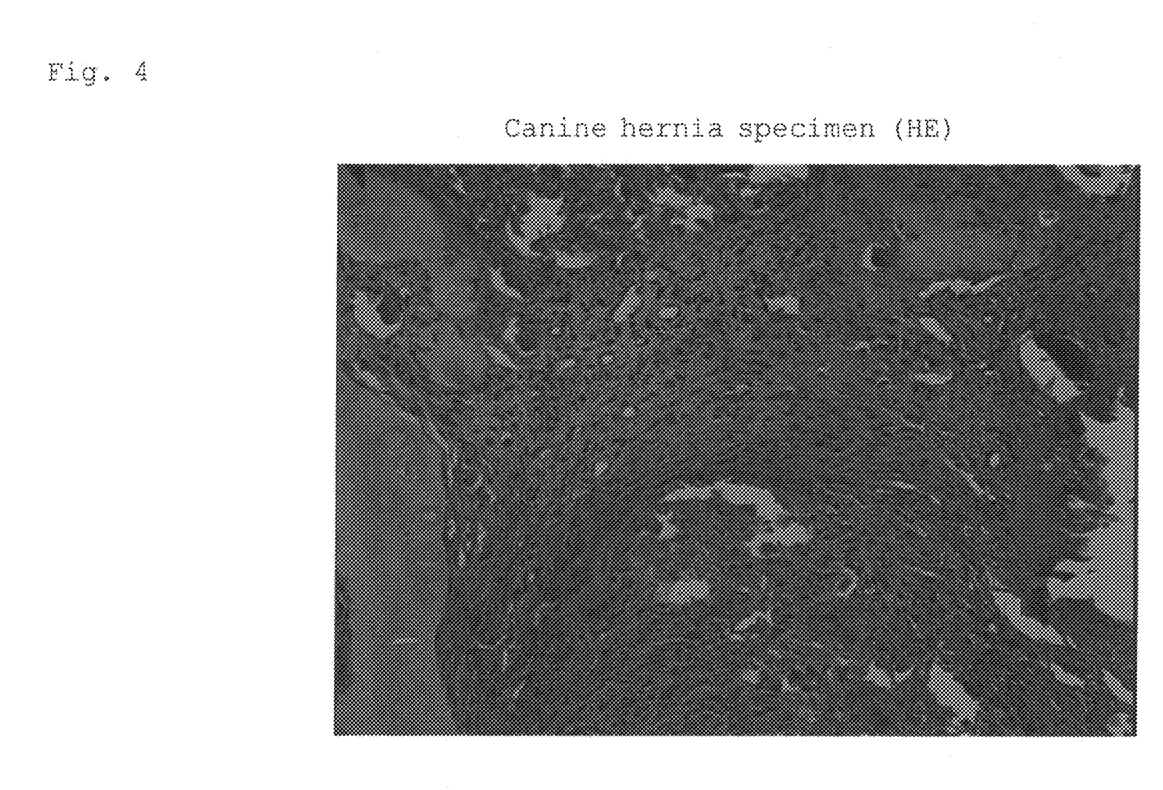
FIG. 4 is a micrograph of a herniated disc tissue sample (hematoxylin-eosin stained) extracted from spontaneous herniated disc from a miniature dachshund.

Dogs, and particularly beagles, have a high incidence of herniated disc, exhibiting paralysis of both of the lower limbs in severe cases. The histology of canine herniated disc is highly similar to the histology of human herniated disc. A sample was prepared from tissue surgically extracted from the 1st/2nd lumbar herniated disc of a 7-year-old, 6.35-kg miniature dachshund that had suffered herniated disc and lower limb paralysis, and was hematoxylin-eosin stained and imaged on a micrograph, shown in FIG. 4. This tissue sample demonstrates that canine herniated disc is highly suitable as a model for human herniated disc.

Drug agents were injected into the herniated discs of beagles with spontaneous herniated disc, and the effects were examined in the following manner. A 7-year-old, 12.75-kg beagle was used for a human recombinant MMP-7 test, and a 7-year-old, 14.4-kg beagle was used for a human recombinant MMP-3 test. The disc was imaged by MRI before injection of the drug agent, to confirm normal disc height, height of degeneration and height of herniated disc.

Administration of MMP-7: The beagle was injected with 20 μg/200 μl into the disc between the 12th thoracic vertebra (T12) and 13th thoracic vertebra (T13), and with 10 μg/100 μl into the disc between the 13th thoracic vertebra (T13) and 1st lumbar vertebra (L1) and the disc between the 1st lumbar vertebra (L1) and 2nd lumbar vertebra (L2). As a control, 200 μl of normal saline was injected into the disc between the 2nd lumbar vertebra (L2) and third lumbar vertebra (L3).

Administration of MMP-3: The beagle was injected with 10 μg/100 μl into the disc between the 11th thoracic vertebra (T11) and 12th thoracic vertebra (T12), with 20 μg/200 μl into the disc between the 12th thoracic vertebra (T12) and 13th thoracic vertebra (T13), and with 10 μg/100 μl into the disc between the 13th thoracic vertebra (T13) and 1st lumbar vertebra (L1). As a control, 200 μl of normal saline was injected into the disc between the 10th thoracic vertebra (T10) and 11th thoracic vertebra (T11).

Figure 5:
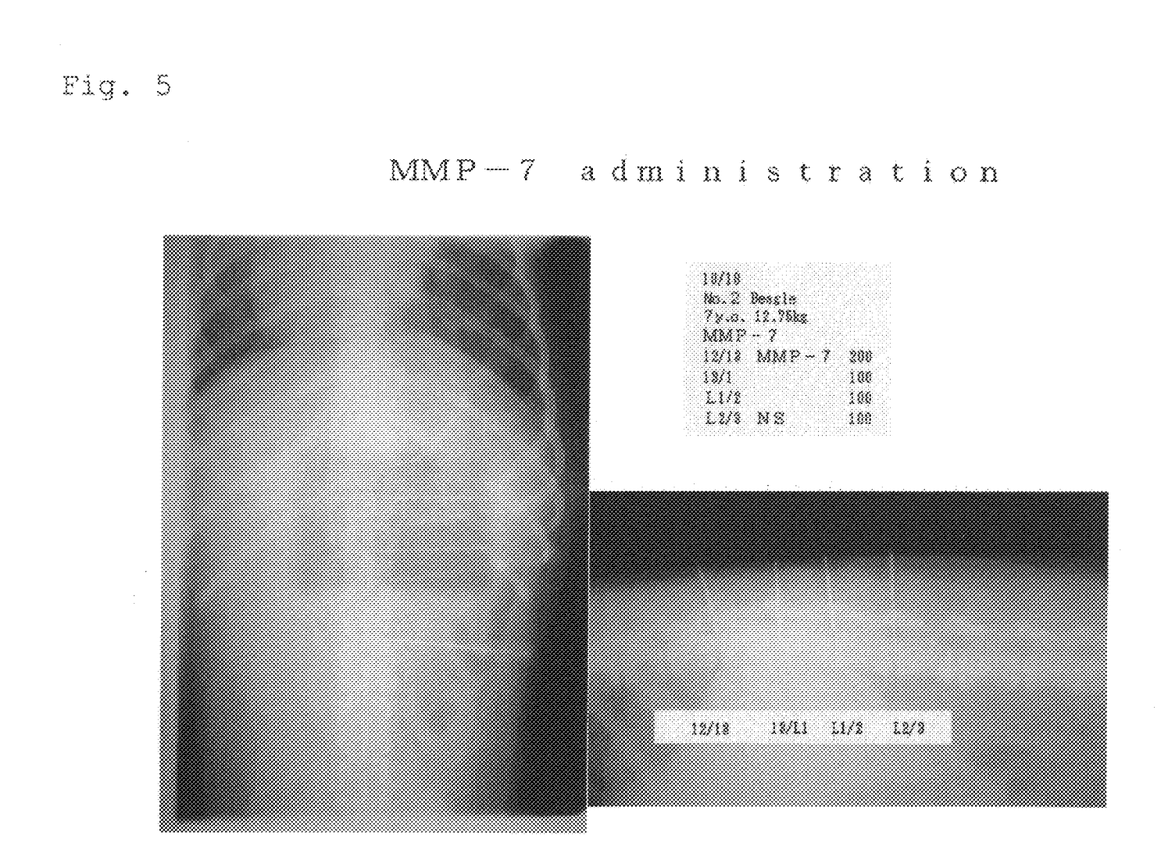
FIG. 5 is a fluoroscopic image showing beagle spontaneous herniated disc upon injection of MMP-7.

Injection of the agents into the intervertebral discs was accomplished using a spinal needle under fluoroscopic control (FIG. 5). The syringe used was a tuberculin syringe (total volume: 1 ml). MRI measurement was repeated one week after injection. The MRI images of the discs before and after injection are shown in FIGS. 6 to 8.

Figure 6:
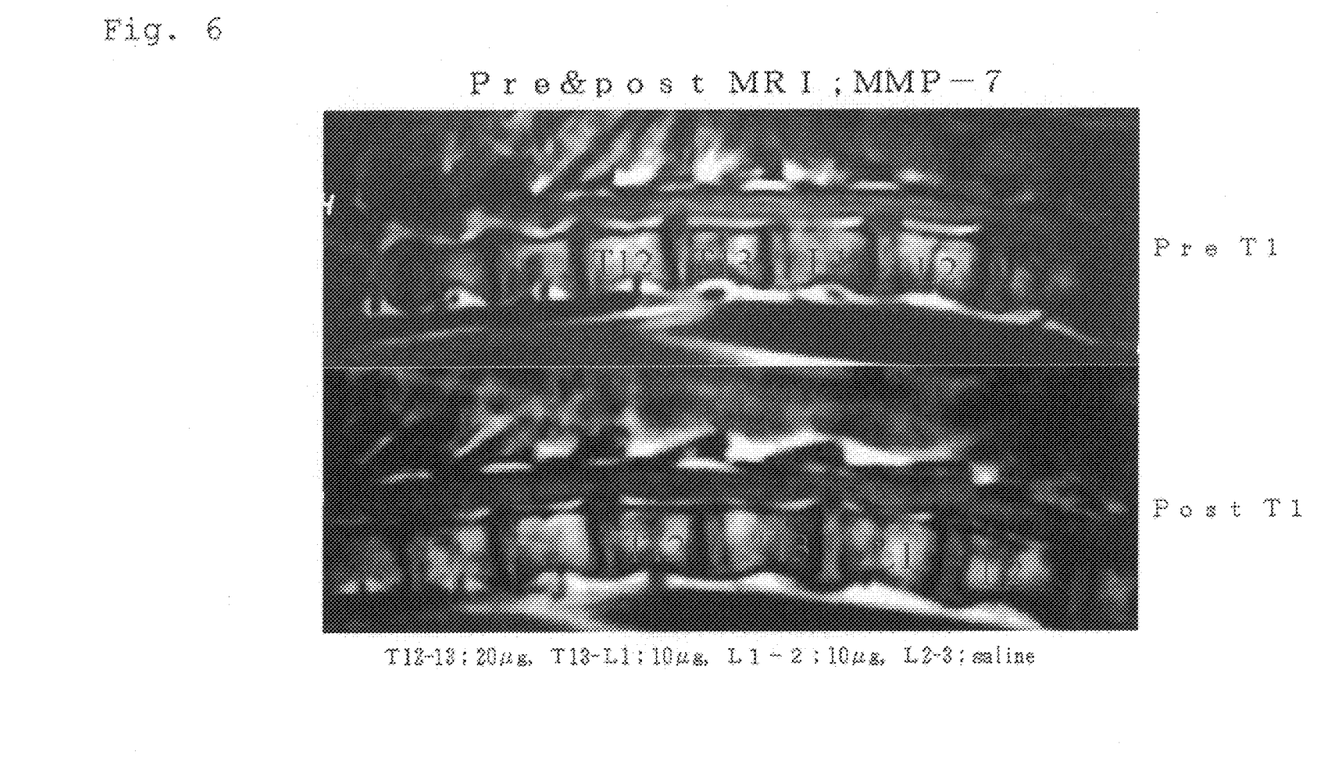
FIG. 6 is a pair of images from MRI (lipid T1-weighted) before (Pre) and after (Post) injection of MMP-7 into beagle spontaneous herniated disc.
Figure 7:
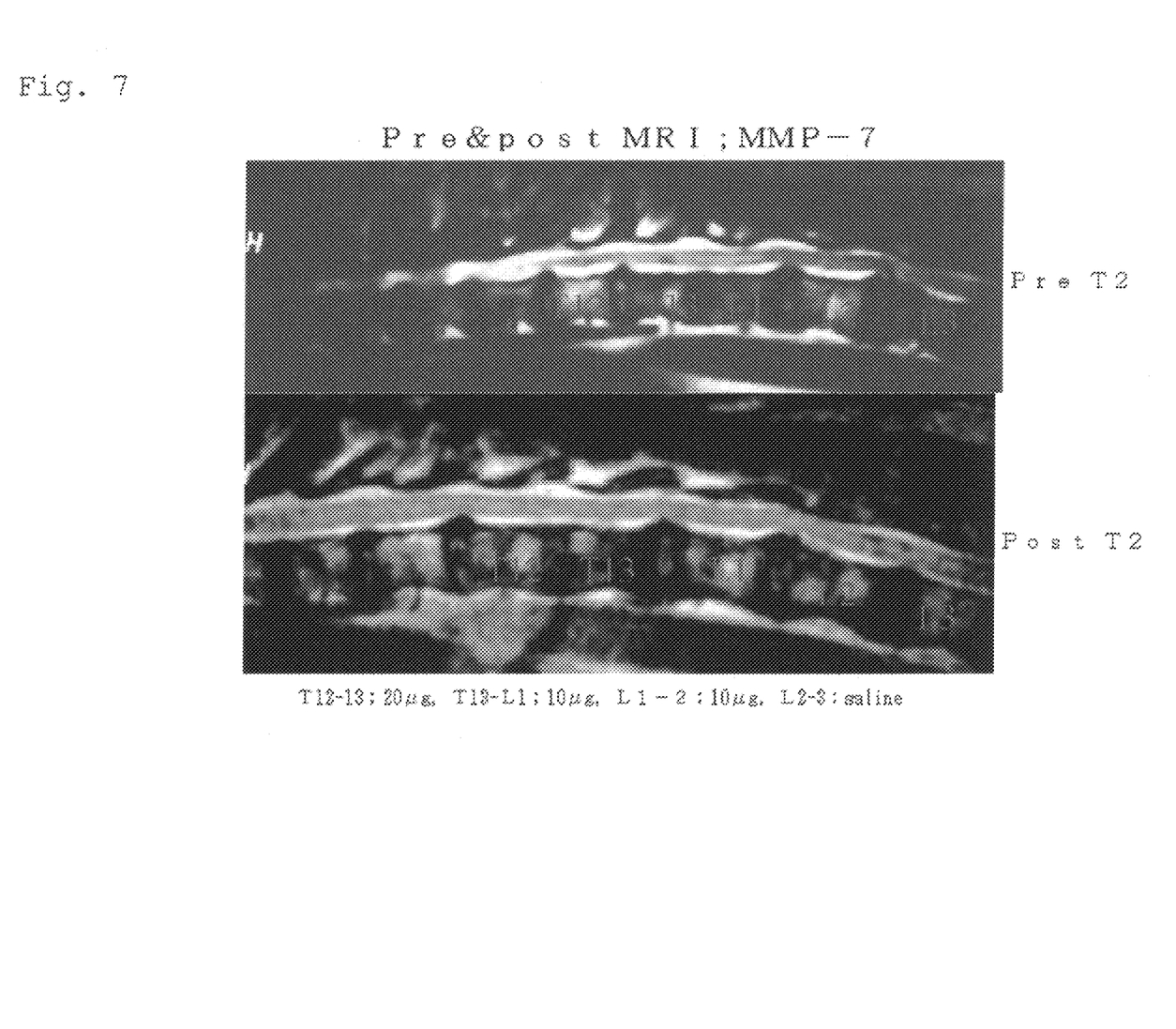
FIG. 7 is a pair of images from MRI (water T2-weighted) before (Pre) and after (Post) injection of MMP-7 into beagle spontaneous herniated disc.
Figure 8:
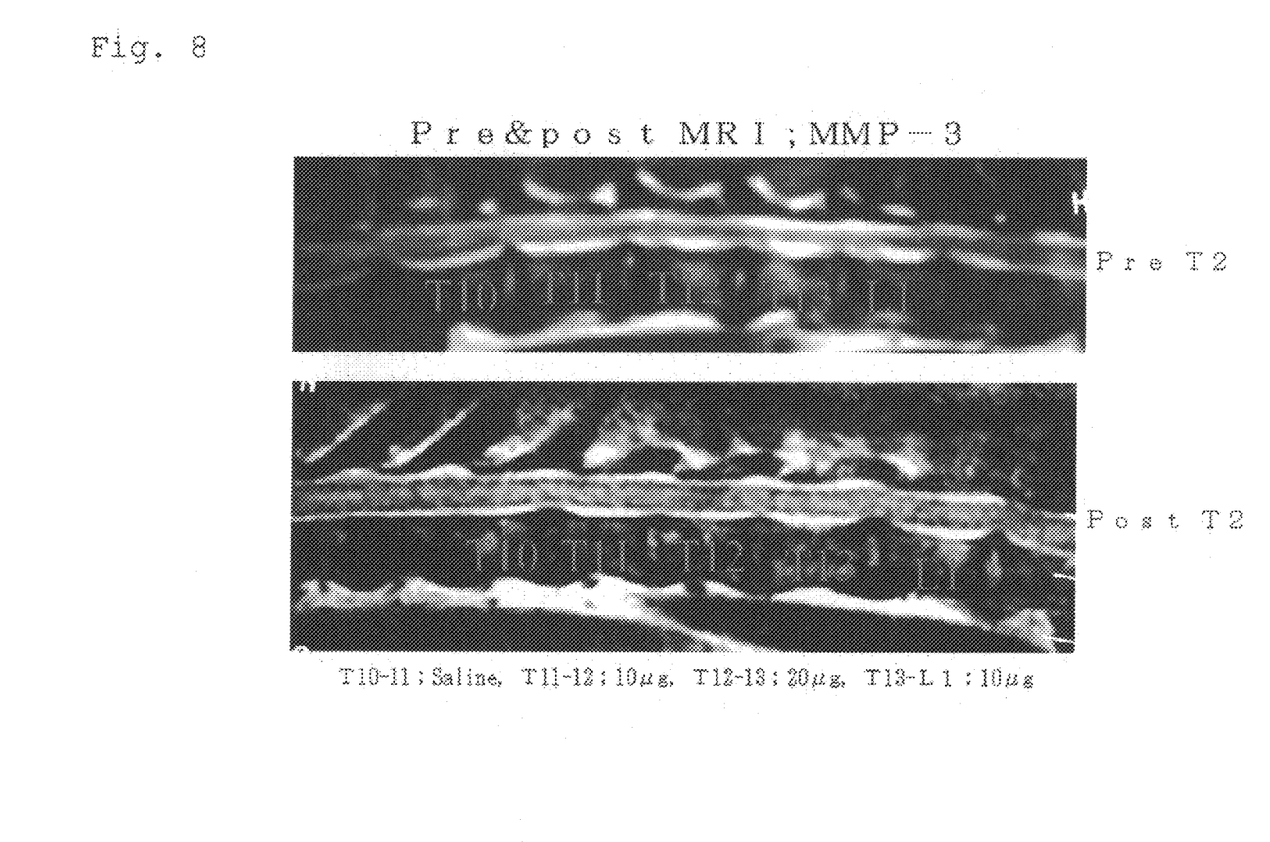
FIG. 8 is a pair of images from MRI (water T2-weighted) before (Pre) and after (Post) injection of MMP-3 into beagle spontaneous herniated disc.

FIG. 6 is a pair of T1-weighted MRI images showing the results using MMP-7. and FIG. 7 is a pair of T2-weighted MRI images showing the results using MMP-7. T1-weighted images are effective for visualizing actual herniated disc, while T2-weighted images are effective for visualizing resolution of the cartilage tissue of intervertebral discs. The herniated disc observed between T12 and T13 before injection has clearly undergone resorption in the image after injection. FIG. 8 is a pair of water content T2-weighted images showing the results using MMP-3, in which resorption of the herniated disc due to injection of the agent is observed.

Figure 9:
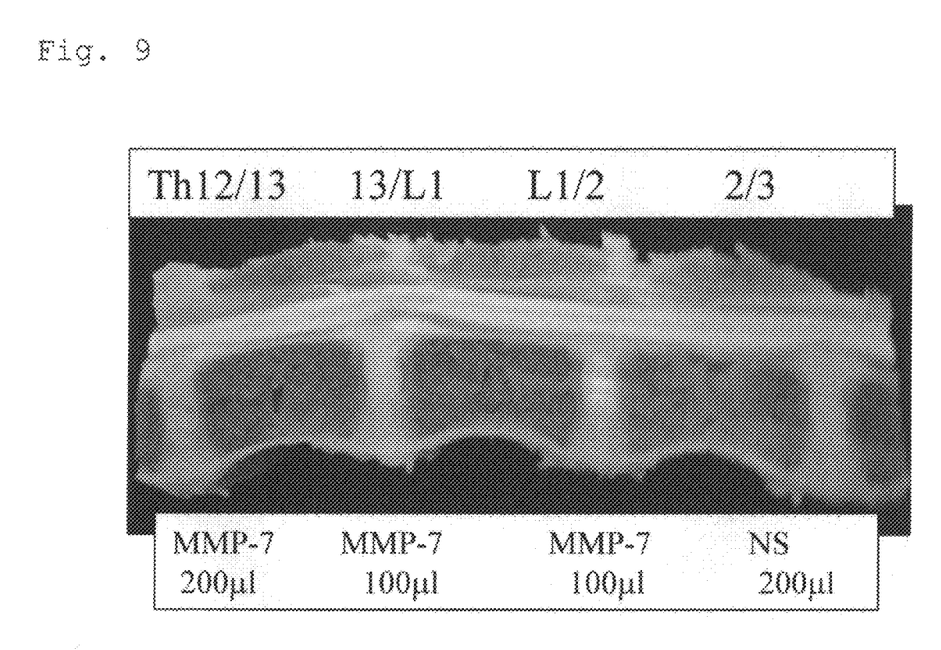
FIG. 9 is a photograph showing cut vertebral samples prepared by injecting MMP-7 and a normal saline as a control into beagle spontaneous herniated discs, and sacrificing after one week.

The MMP-7 administered beagle was then sacrificed, and the vertebral unit comprising the injected disc was extracted en bloc, fixed with a 4% paraformaldehyde solution and subjected to a decalcification procedure, after which a tissue sample was prepared (FIG. 9). Specifically, fixing with the 4% paraformaldehyde solution was followed by rinsing with 10 mM PBS and delipidization with ethanol and chloroform. Next, a decalcified solution (Plank Rychlo method: Wako, Japan) was used for a decalcification procedure. Upon confirming adequate decalcification, paraffin embedding was performed to obtain a tissue sample.

After deparaffinization of the tissue sample, it was stained for 5 minutes with 0.03% Fast Green dissolved in 1% aqueous acetic acid. After then washing with 1% aqueous acetic acid, it was further stained for 7 minutes with 0.25% Safranin O.

Figure 10:
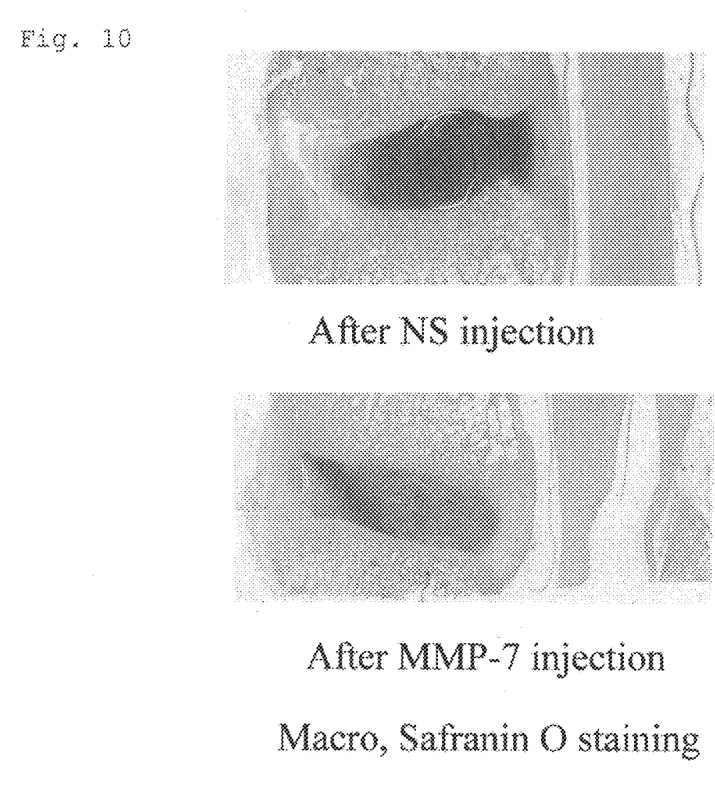
FIG. 10 is a pair of photographs showing the results of Safranin O staining of vertebral samples prepared by injecting MMP-7 and normal saline as a control into beagle spontaneous herniated discs, and then sacrificing after one week; the results are shown for injection of MMP-7 and injection of normal saline.
Figure 11:
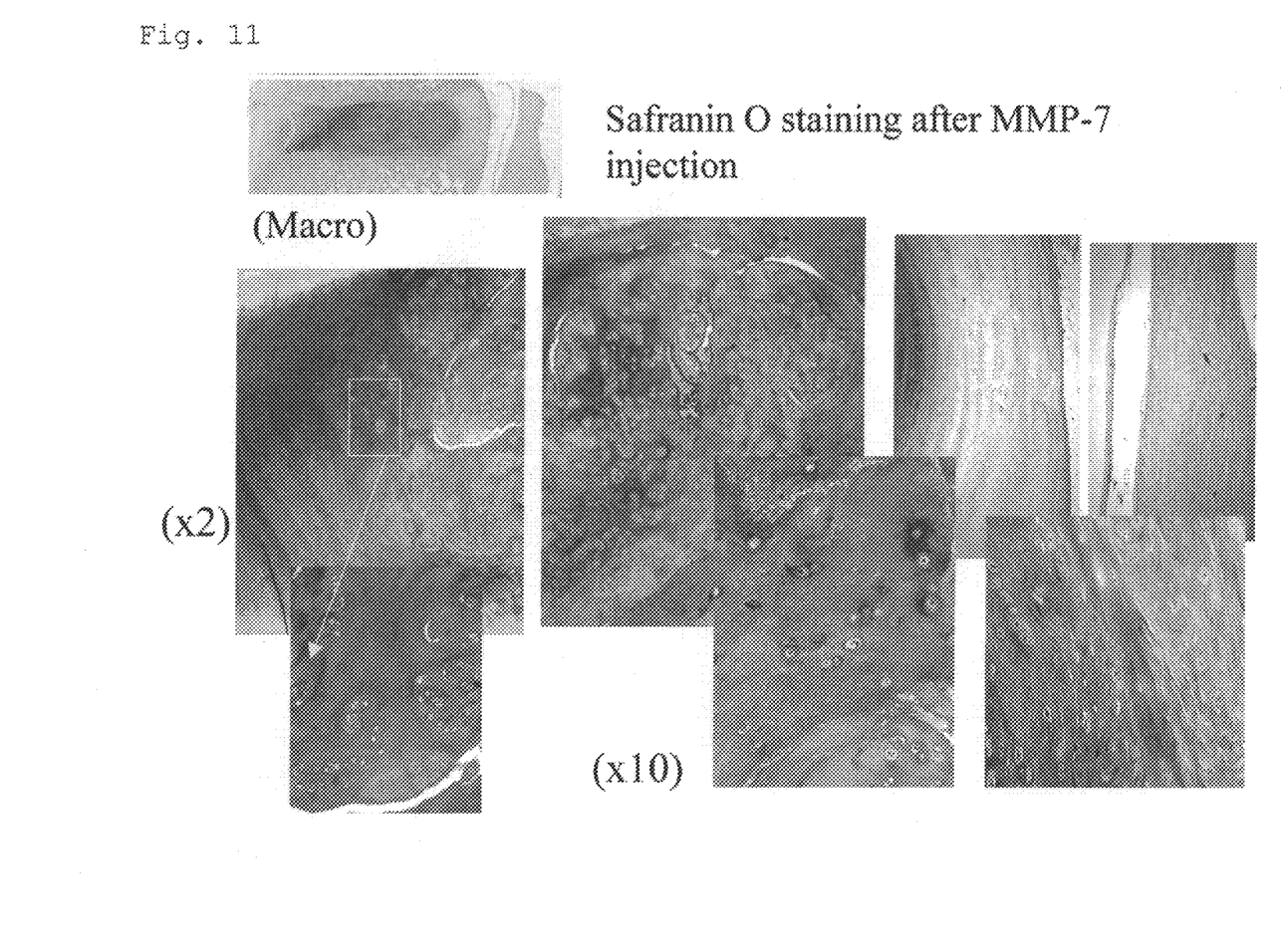
FIG. 11 is a photograph showing the results of Safranin O staining of a vertebral sample prepared by injecting MMP-7 into beagle spontaneous herniated disc, and sacrificing after one week.
Figure 12:
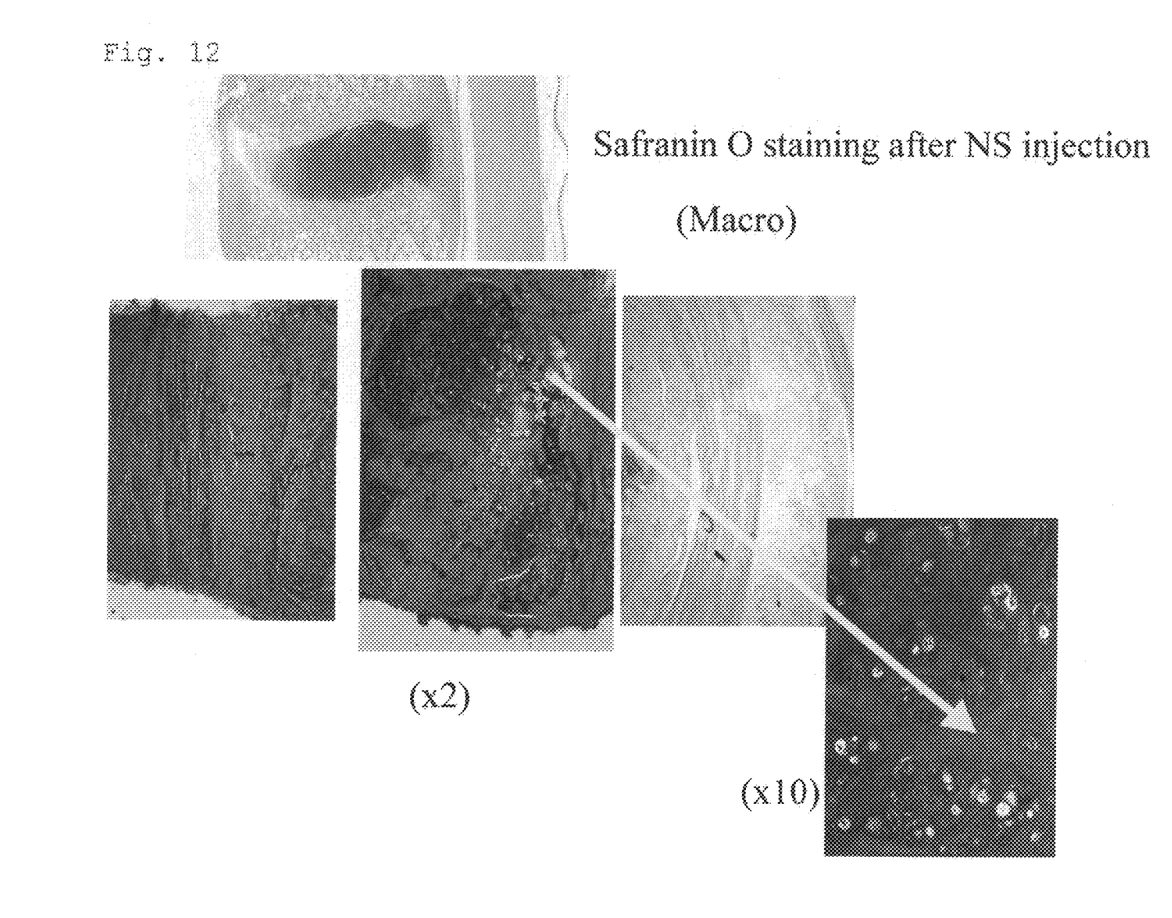
FIG. 12 is a photograph showing the results of Safranin O staining of a vertebral sample prepared by injecting normal saline as a control into beagle spontaneous herniated disc, and sacrificing after one week.

FIG. 10 shows photographs of strips thereof (macro image). The strip labeled "After MMP-7 injection" is a strip from the location injected with 200 μl of MMP-7 (12th and 13th thoracic vertebrae), and the strip labeled "After normal saline injection" is a strip taken from between the 2nd and 3rd lumbar vertebrae injected with normal saline. The strips are shown in greater detail in FIGS. 11 and 12. FIG. 11 shows the strip injected with MMP-7, together with the same macro image at the bottom of FIG. 10 shown at the upper left corner. The macro image is shown at 2× magnification at the middle of the page, and a portion of the 2× magnified image is shown at additional 10× magnification at the bottom of the page. FIG. 12 shows the strip injected with normal saline, with the macro image shown at the upper left corner, 2× magnification at the middle, and 10× magnification at the bottom. When FIG. 10, FIG. 11 and FIG. 12 are compared, it is seen that injection of MMP-7 significantly reduced staining compared to normal saline. This indicates that the MMP-7 injection had destroyed the structure of the nucleus pulposus. In contrast, disturbance of the nucleus pulposus structure with injection of normal saline was found only at the site of injection, and staining was unchanged. Thus, no destruction of the cartilaginous matrix was found.

In FIG. 11 showing the results of MMP-7 injection, the nucleus pulposus injected with MMP-7 appears as a degraded matrix, but normal chondrocytes were preserved in the other nucleus pulposus areas and in the annulus fibrosus. Thus, it was concluded that the normal chondrocytes retained their function of producing the cartilaginous matrix and regenerating the intervertebral disc.

Example 4

Molecular Biological Examination Using Canine Herniated Disc

In the same manner as Example 3, a beagle (7-year-old, 14.0 kg body weight) with spontaneous herniated disc was injected with 20 μg/200 μl of MMP-7 into the disc between the 2nd cervical vertebra (C2) and 3rd cervical vertebra (C3), and with 200 μl of normal saline into the disc between the 3rd cervical vertebra (C3) and 4th cervical vertebra (C4). The protein was extracted from the discs one week after injection, and human adult cartilage proteoglycan antibody was used for molecular biological examination of intervertebral disc cartilage degradation by Western blotting. Cross-reaction of human adult cartilage proteoglycan antibody with canine has been confirmed, and the antibody has been demonstrated to recognize the core protein and keratan sulfate side chain.

After sacrificing the beagle, the vertebral unit was immediately extracted and stored in ice. Next, the intervertebral tissue at the target site was carefully separated using a scalpel or the like to avoid contamination with the surrounding tissue. The sampled tissue was placed in a 10 cm dish, and then a solution comprising one proteinase inhibitor tablet (Roche: proteinase inhibitor cocktail tablet) dissolved in 4 ml of RIPA (Radio Immuno Precipitation Assay) buffer solution was added and crushed in the dish. The composition of the RIPA buffer solution was 50 mM Tris-HCl buffer (pH 8.0) containing 150 mM NaCl, 1% Triton-100, 0.5% sodium deoxycholate and 0.1% SDS. After stirring overnight at 4° C., the solution in the dish was taken and centrifuged at 4° C., 3000 rpm for 5 minutes. The supernatant was used as a protein extract for the experiment.

As a positive control to contrast with the beagle intervertebral disc protein, there was used protein extracted from normal human knee cartilage obtained during surgical removal of a bone tumor surrounding the knee joint.

Figure 13:
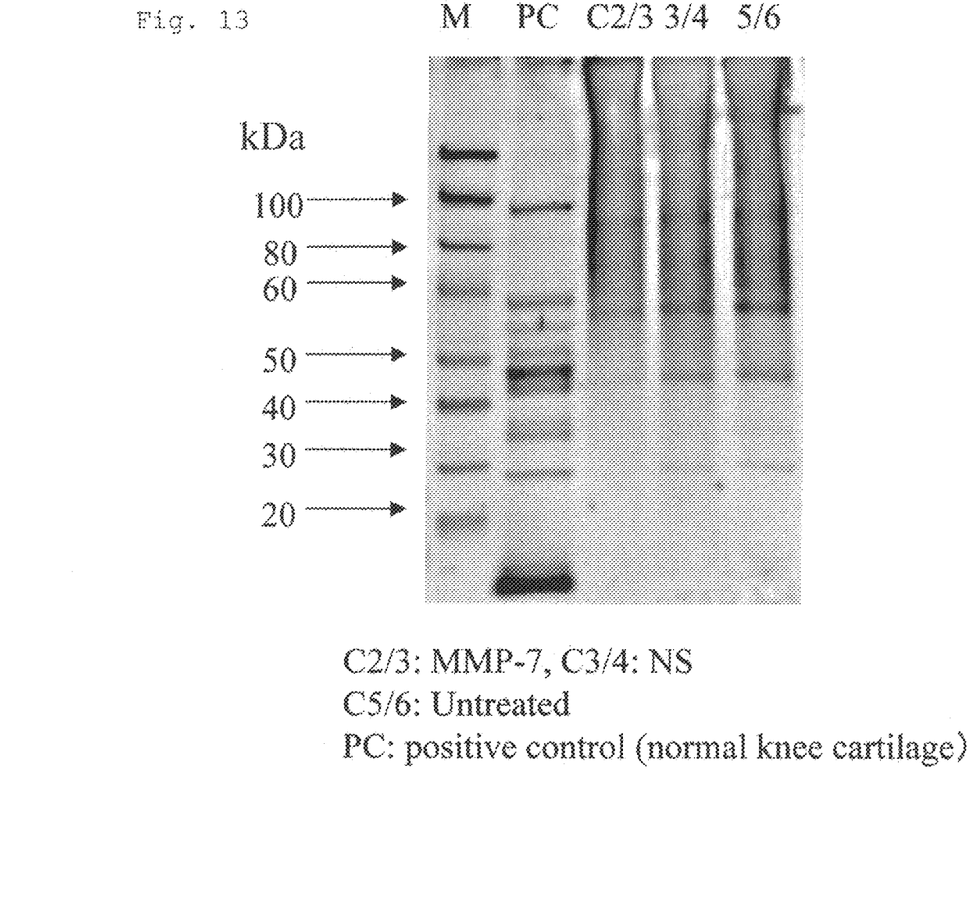
FIG. 13 is an image showing the results of a Western blot for testing of proteoglycan degradation by MMP-7.

The concentration of each protein extract solution was adjusted by protein assay, and then Laemmli Sample Buffer was added, the mixture was boiled at 95° C. for 3 minutes, and SDS-PAGE (80 V, 180 min) was carried out using 12% gel (PAG Minigel, Daiichi Pure Chemicals). It was then transferred to a nitrocellulose membrane (0.1 A, 45 min). After then reacting it with human adult cartilage proteoglycan antibody by Chemicon (Temecula, Calif., USA), the product was colored with an ECL kit (Amersham Pharmacia Biotech, UK). The results are shown in FIG. 13. In the photograph, M represents a molecular weight marker, PC represents the positive control using protein extracted from normal human knee cartilage, C2/3 represents protein extracted from MMP-7 injected intervertebral disc, C3/4 represents protein extracted from normal saline injected intervertebral disc, and C5/6 represents protein extracted from an untreated intervertebral disc (between the 5th and 6th cervical vertebrae).

The bands from 40 kDa to 100 kDa represent the G1 domain-containing core protein and keratan sulfate side chains. The lack of one single band reflects the presence of several decomposition products due to proteoglycan decomposition by physiological enzymes, since the specimen was a clinical specimen. In the case of the positive control (PC) which used protein extracted from normal human knee cartilage, various proteoglycan-degrading enzymes such as MMPs and aggrecanase were present and therefore proteoglycan decomposition products were detected. Proteoglycan decomposition products were also detected with normal saline injection (C3/4) and the untreated sample (C5/6). In comparison, MMP-7 injection clearly reduced the amount of proteoglycan decomposition products. This result demonstrates that MMP-7 had degraded the proteoglycan in the herniated disc.

The organ culturing experiment using a surgically removed herniated disc specimen (Example 1) clearly demonstrated that herniated disc is degraded by MMP-3 and MMP-7. Also, the experiment of injection into rabbit intervertebral disc (Example 2), the experiment of injection into beagle spontaneous herniated disc (Example 3) and the molecular biological examination using canine herniated disc (Example 4) clearly showed that degradation of the intervertebral disc and herniated disc matrix occurs by intervertebral disc injection of MMP-3 and MMP-7. These findings confirmed that MMP-3 and MMP-7 are effective for treatment of herniated disc.

Reference Example

Figure 14:
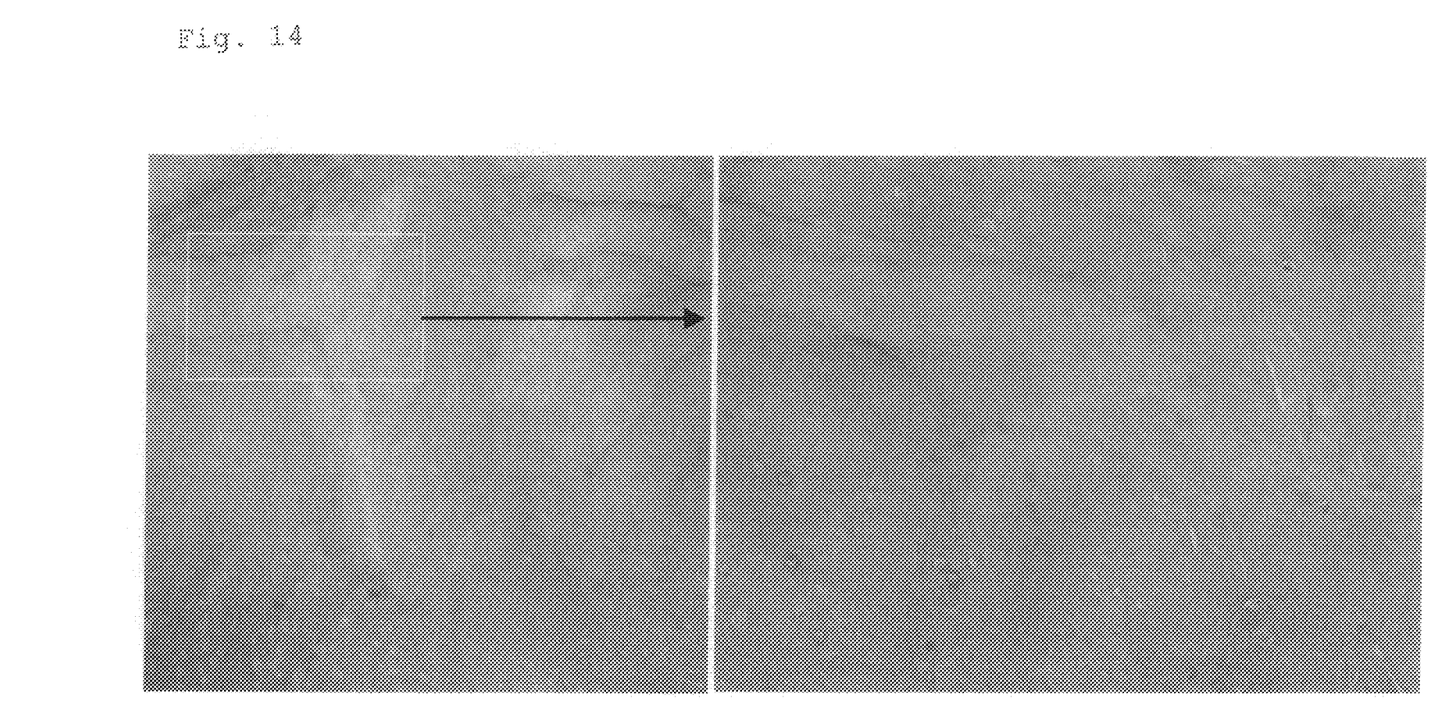
FIG. 14 is an image showing the results of Safranin O staining of a pathological sample prepared by injecting chymopapain into canine herniated disc, and sacrificing after one week after injection.

One week after injection of chymopapain into the herniated disc of a canine, it was sacrificed and a pathological sample was prepared and stained in the same manner as Example 3. Photographs are shown in FIG. 14. In this case, the cartilaginous matrix was degraded throughout the entire nucleus pulposus and annulus fibrosus, with very few surviving chondrocytes. Thus, it was concluded that injection of chymopapain into the site of herniated disc produces injury to normal chondrocytes, thereby reducing the intervertebral disc regenerative capacity in comparison to injection of MMP-7 according to the invention.

INDUSTRIAL APPLICABILITY

The agent for treating diseases associated with degenerative intervertebral disc according to the invention, whereby a human-derived protease such as MMP-3 and MMP-7 is directly administered to the site of a disease associated with degenerative intervertebral disc, allows such diseases to be cured rapidly. The diseases include, for example, herniated disc, lumbago, discopathy and spondylosis. Human-derived proteases are highly superior to plant-derived enzymes such as chymopapain which have been conventionally applied in the clinic, in that they do not cause serious immunoreactions such as anaphylaxis, and do not injure normal chondrocytes.

The invention claimed is:

1. A method for treating a herniated disc or herniated nucleus pulposus in a mammal, consisting essentially of administering MMP-7 to the affected site of the herniated disc or herniated nucleus pulposus in said mammal.

2. A method for treating a herniated disc or herniated nucleus pulposus in a mammal, consisting of administering MMP-7 and a pharmaceutically acceptable carrier to the affected site of the herniated disc or herniated nucleus pulposus in said mammal.

* * * * *